United States Patent [19]

Hadden

[11] Patent Number: 5,632,983
[45] Date of Patent: May 27, 1997

[54] METHOD FOR TREATING SECONDARY IMMUNODEFICIENCY

[75] Inventor: John W. Hadden, Tampa, Fla.

[73] Assignee: University of South Florida, Tampa, Fla.

[21] Appl. No.: 341,424

[22] Filed: Nov. 17, 1994

[51] Int. Cl.$^6$ .......................... A61K 38/19; A61K 45/05
[52] U.S. Cl. .................. 424/85.1; 424/85.2; 424/85.4; 514/21
[58] Field of Search ................. 424/85.1, 85.2, 424/85.3, 85.4, 85.5; 514/2, 12, 21; 530/350, 351

[56] References Cited

U.S. PATENT DOCUMENTS

| | | | |
|---|---|---|---|
| 4,116,951 | 9/1978 | Wang | 530/324 |
| 4,353,821 | 10/1982 | Birr et al. | 530/324 |
| 4,466,918 | 8/1984 | Birr et al. | 530/334 |
| 4,470,926 | 9/1984 | Birr et al. | 530/329 |
| 4,612,365 | 9/1986 | Birr et al. | 530/329 |
| 4,659,694 | 4/1987 | Horecker | 514/12 |
| 4,716,148 | 12/1987 | Horecker | 514/12 |
| 4,910,296 | 3/1990 | Birr et al. | 530/324 |
| 5,093,114 | 3/1992 | Rideout et al. | 424/85.4 |
| 5,114,711 | 5/1992 | Bell et al. | 424/85.1 |

OTHER PUBLICATIONS

*The Investigator's Handbook* provided by the Cancer Therapy Evaluation Program, Division of Cancer Treatment, National Cancer Institute, p. 22.

Belldegrun and Rosenberg, "Adoptive immunotherapy of urologic tumors", *Cancer Treat. Res.* 46:213–233, 1989.

Borden, "Interferons: rationale for clinical trials in neoplastic disease", *Ann. Int. Med.* 91:492–479, 1979.

Chang and Rosenberg, "Overview of interleukin-2 as immunotherapeutic agent", *Semin. Surg. Oncol.* 5(6):385–390, 1989.

Chirigos and Talmadge, "Immunotherapeutic agents: their role in cellular immunity and their therapeutic potential" *Springer Seminars in Immunopathol.* 8:327–336, 1985.

Cortesina et al., "Treatment of recurrent squamous cancer cell of head and neck with low doses of interleukin 2 injected . . . " *Br. J. Cancer* 62:2482–2485, 1988.

Cortesina et al., "Temporary regression of recurrent squamous cell carcinoma of the head and neck is achieved with a low . . . " *Br. J. Cancer* 69:572–576, 1994.

DeSimone et al., "Report of the symposium on the use of intravenous gammaglobulin (IVIG) in adults infected with HIV" *J. Clin. Lab. Anal.* 4:313–317, 1990.

Devos, *Nucleic Acids Res.*, 11:4307–4323, 1983.

Frillingos et al., "Appearance of thymosin α in supernatants of monocytes . . . " *Archives of Biochemistry and Biophysics*, vol. 296, No. 1, Jul., pp. 356–363, 1992.

Goldstein et al., *Proc. Natl. Acad. Sci.*, 74(2):725–729, Feb. 1977.

Goldstein and Laslo, "The role of interferon in cancer therapy: a current perspective" *Ca–A Cancer Journal for Clinicians* 38:258–290, 1988.

Goldstein, in *Combination Therapies 2*, pp. 39–48, Plenum Press, NY, 1993.

Hadden et al., "Strategies of immune reconstitituion: effects of lymphokines . . . " *Life Sci.* 44:V–XII, 1989.

Hadden et al., "The characterization of immunotherapeutic agents" *Immunopheron Reviews* 1:1–64, 1992.

Hadden, "Immunotherapy of human immunodeficiency virus infection" *TIPS Reviews*, 1991.

Hadden, "Thymic Endocrinology" *Int. J. Immunopharmacol.* 14:345–352, 1992.

Hadden and Smith, "Immunopharmacology" *JAMA*, 268:2964–2969, 1992.

Hadden et al., *Cell. Immunol.* 144:228–236, 1992.

(List continued on next page.)

*Primary Examiner*—Ponnathapura Achutamurthy
*Attorney, Agent, or Firm*—Kohn & Associates

[57] ABSTRACT

A method of treating cellular immune deficiency in a patient including the steps of determining the presence of a cellular immune deficiency and co-administering to the patient an effective amount of a thymic peptide combined with an effective amount of an immunomodulating natural nonrecombinant cytokine preparation.

2 Claims, 3 Drawing Sheets

OTHER PUBLICATIONS

Hadden "Immunostimulants" *Immunology Today 276*, vol. 14, No. 6, 1993.

Hadden et al., *Arch. Otolaryngol.* 120:395–403, 1994a.

Hwu and Rosenberg, "The genetic modification of T cells for cancer therapy: an overview . . . " *Cancer Detect. Prev.* 18(1):43–50, 1994b.

*IGIV News Update*, "An extra measure of viral safety", vol. 1, No. 2, Dec. 1993.

Kameda et al., "Mixed lymphokines in low does prolong life in cyclophosphamide–treated melanoma–bearing mice" *Int. J. Immunother.* 8:1–5, 1992.

Lane and Fauci, "Therapeutic approaches to the underlying immune deficit in AIDS" *Abstracts Int. Conf. on AIDS*, Paris, 1986.

Maric et al., "Immunostimulatory activity of prothymosin–alpha in senescence" *Annals New York Academy of Science*, pp. 148–158.

Mattijssen, "Clinical and immunopathological results of a phase II study . . . " *J. Immunother.* 10:63–68, 1991.

Merigan, "Combination anti HIV therapy in combinaton therapy 2" eds. Garaci and Goldstein, Plenum Press, pp. 225–229, 1993.

Mishell and Shiigi, Selected Methods in Cellular Immunology, Freeman, pp. 23–24, 1981.

Morgan et al., "Selective in vitro Growth of T lymphocytes from normal human bone marrows" *Science* 193:1007–8, 1976.

Mule and Rosenberg, "Mechanistic aspects of successful immunotherapy . . . " *Prog. Clin. Biol.*, 244:79–91, 1987.

Mutch and Hutson, "Levamisole in the adjuvant treatment of colon cancer", *Clin. Pharmacol.* 10:95–109, 1991.

Paetkeau et al., *J. Immunol.* 117:1320–4, 1976.

Pulley et al., "Intravenous, intralesional and endolymphatic adminstration of lymphokines in human cancer" *Lymphokine Research*, vol. 5, Supp. 1, pp. S157–163, 1986.

Rosenberg, et al., "Observations on the systemic adminstration of autologous lymphokine–activated killer cells and recombinant . . . " *New. Eng. J. Med.* 313:1485–1492, 1985.

Rosenberg et al., "A progress report on the treatment of 157 patients with advanced cancer . . . " *N. Engl. J. Med.* 316:889–897, 1987.

Rosenberg, "Immunotherapy of cancer by systemic adminstration of lymphoid cells plus interleukin–2" *J. Biol. Resp. Mod.* 3:501–511, 1994.

Shuloff, "Thymic peptide hormones: basic properties and clinical applications in cancer" *CRC Critical Reviews in Oncology/Hematology*, 3:3309–276, 1985.

Spreafico, "Use of levamisole in cancer patients" *Drugs* 19:105–116, 1980.

Symoens and Rosenthal, "Levamisole in the modulation of immune response: the current experimental and clinical state" *J. Reticuloendothel. Soc.* 21:175–219, 1977.

Talmadge et al., "Screening for biological response modifiers: methods and rationale" Martinus Nijhoff, Boston, pp. 121–129 and pp. 181–182, 1985.

Tanigushi et al., "Structure and expression of a cloned cDNA for human interleukin–2" *Nature*, 302:305–310, 1983.

Webb et al., "Mitogen–induced human lymphocyte activation in serum–free medium" *Clinical Immunology and Immunopathology*, 1:304–310, 1973.

Kovacs et al., "Increases in CD4 T lymphocytes with intermittent courses of interleukin–2 . . . " *New Eng. J. Med.* 332:567–575, 1995.

METHOD FOR TREATING SECONDARY IMMUNODEFICIENCY

TECHNICAL FIELD

The present invention relates to an improved method of treating cellular immune deficiencies.

BACKGROUND OF THE INVENTION

In recent years it has become possible to modulate the immune system to improve its response and, where components of the system are non-functioning, to either partially or completely restore the function of the component. For example, bone marrow transplantation is used to replace stem cells or provide missing stem cells to cure severe combined immunodeficiency. In another example, immune cells are removed from cancer patients, treated, and returned to the patient wherein there is tumor regression. (Hwu and Rosenberg, 1994a; Hwu and Rosenberg, 1994b) Further, components of the humeral immune system such as γ-globulin and intravenous immunoglobulin (IVIG) are finding wide therapeutic applications (DeSimone et al., 1990; Hall, 1993). Other immune system components and agents are also being used as therapeutics. (Hadden & Smith, 1992; Hadden, 1993).

Immunomodulators are compounds that modify immune function or have a positive or negative effect on the activity of the immune system. The use of immunomodulators in clinical medicine includes the reconstitution of immune function (or the correction of immunodeficiency) and the suppression of normal or excessive immune function. A major class of immunomodulators is cytokines. Through recombinant technology, many of the cytokines are now available. However, the immune system is complex and the interaction of various components is often necessary to effectively modify immune functions. It would be useful to design preparations that provide the various components and interactions to effectively regulate immune function.

Cytokines are peptide/protein immunomodulators that are produced by activated immune cells including thymus-derived T lymphocytes (T-cells), B lymphocytes and monocyte/macrophages. The cytokines include interleukins (IL-1 through IL-15), colony stimulating factors (CSFs) for granulocytes and/or macrophages (CSF-G, CSF-M, CSF-GM), tumor necrosis factors (TNFs α & β), and interferons (IFN α, β & γ).

Interleukin-2 (IL-2) is a lymphokine initially described as a T-cell growth factor (Morgan et al., 1976) IL-2 induces and supports proliferation of antigen or mitogen stimulated T-cells. In addition to the T lymphocyte stimulating function, IL-2 is important in such processes as the initiation, expansion and regulation of the immune response, the production of gamma-interferon (IFNγ), the induction of lymphokine-activated killer (LAK) cells, the propagation of cytolytic T-cells, and the augmentation of the killer activity of natural killer (NK) cells. Recombinant IL-2 (rIL-2) is a non-glycosylated protein that is produced by the human cDNA sequence (Taniguchi et al., 1983; Devos, 1983; U.S. Pat. Nos. 4,604,327, 4,569,790 and 4,518,584)

Various individual cytokines, both natural and recombinant, have been investigated for the treatment of cancer and other diseases. For example, recombinant interferon $\alpha_2$ (rIFN $\alpha_2$) is approved by the U.S. Food & Drug Administration (FDA) for treatment of Hairy cell leukemia, Kaposi's sarcoma, condyloma accuminata, and chronic hepatitis. Natural IFNαs, as a mixture (Alferon®) of the twenty or more made by leukocytes, is licensed for condyloma accumenata. Recombinant IFN-γ(rIFN-γ) is licensed for chronic granulomatous disease. rIL-2 is licensed for renal cell cancer. These and other rIL's and rIFNs are under active evaluation in a variety of diseases including several forms of cancer.

Further, rIL-2 cancer therapy has been explored in many clinics and research centers. Rosenberg and colleagues (Rosenberg et al. 1985, 1987; Mulé and Rosenberg, 1987; Chang and Rosenberg, 1989; Belldegrun and Rosenberg, 1989 and Rosenberg, 1994) have reported the use of systemically administered rIL-2 in the immunotherapy of patients with renal cell cancer, pulmonary cancer and melanoma. Cortesina et al. (1988, 1994) described the effects of loco-regional injections of natural and rIL-2 in head and neck cancer patients and found natural IL-2 to be more effective in yielding tumor regression. Also, patients given large doses of rIL-2 have suffered life threatening toxicity. (Rosenberg et al., 1987).

The development and commercial availability of genetically (recombinant) engineered immunomodulators has accelerated the evaluation of these agents in the cancer clinic. The limited efficacy and significant toxicity associated with high doses of rIL-2, rIFN-γ, rTNF-α, and other monotherapies, suggests reconsideration of natural combinations of cytokines in therapeutic strategies. Furthermore, more than one-hundred different cytokine activities have been identified, which raises significant doubt as to whether immunotherapy, based upon combining recombinant cytokines, has a reasonable probability of success in the cancer clinic in the near future.

For example, while IL-2 can stimulate T lymphocyte proliferation as a T-cell growth factor, a number of other factors including other interleukins and thymic peptides are produced in the thymus and are also considered necessary for T lymphocyte development and function. (Hadden, 1992).

An uncharacterized natural interleukin preparation (NI) has been shown by applicants to be effective in promoting T lymphocyte development. This uncharacterized mixed preparation (also referred to as buffy coat interleukin, BC-IL) stimulated the proliferation of prothymocytes, immature and mature thymocytes in vitro more effectively than an equivalent concentration of rIL-2 (Hadden et al., 1989). The NI preparation augmented T lymphocyte development in neonatal mice while rIL-2 was inactive (Hadden et al., 1989) and augmented T lymphocyte development and function in hydrocortisone-treated, aged mice while rIL-2 in equivalent dose was inactive (Hadden et al., 1992b). The NI preparation in low dose prolonged the life in mice bearing malignant melanoma; rIL-2 in equivalent dose was inactive (Kameda et al., 1992). These findings indicated that natural interleukins mixtures have activities not provided by IL-2.

Attempts to correct T lymphocyte defects have been tried experimentally in a variety of settings including T lymphocyte depletion (lymphocytopenia) and T lymphocyte dysfunction (anergy) occurring in aging, cancer, AIDS, and other immunodeficiencies. For example, rIL-2 and thymic peptides have been used in AIDS (HIV) virus infection with variable results (Hadden, 1991). High dose rIL-2 by continuous infusion has been shown to transiently increase T lymphocyte counts in blood of patients with HIV infection but with considerable toxicity (Lane and Fauci, 1986). Pegylated rIL-2 at one and three million units yielded less toxicity but only minor effects on lymphocyte counts in humans with HIV infection (Merigan, 1993). An NI preparation significantly augmented T lymphocyte counts in lymphocytopenia cancer patients without toxicity (Hadden et al, 1994). These findings indicate that natural interleukins act in humans in low doses to increase T cells without toxicity and that rIL-2 while active at high doses is too toxic for medical use. These findings also support the extrapolation of murine data to man.

The above indicates that the use of preparations of naturally occurring cytokines combined with other factors may be more efficient in affecting the immune system with less toxicity. However, the preparations that are currently available are not well characterized and are cumbersome to produce. In order to reproducibly modulate the immune system it would be useful to have well characterized preparations of cytokines that can be produced easily and from which it will be possible to establish reproducible low-toxicity dosages. Prior work by the applicant (Hadden et al., 1992a) and the co-pending patent application U.S. Ser. No. 08/610,075 by the same applicant and assigned to the assignee of the present application and incorporated herein by reference provides such natural cytokine preparations (NI, NIM or NCM).

Deficiencies of cellular immunity in man have also been treated with various thymic hormone/peptide preparations e.g. thymostimulin, Thymosin fraction IV, Thymosin $\alpha_1$, zinc-thymulin, thymopoietin, thymopentin, and thymic humoral factor (Shuloff, 1985). Several of these preparations are licensed for clinical use in European countries, especially Italy and Germany.

Thymosin $\alpha_1$ (T-$\alpha$1) is a 28 amino acid peptide initially extracted from bovine thymus and later synthesized. (Goldstein et al., 1977; U.S. Pat. Nos. 4,079,127, 4,148,788, 4,293,455, 4,504,415) Thymosin $\alpha_1$ has been used experimentally to treat cellular immune deficiency and cancer in mice and humans (Goldstein, 1993). It is licensed in Italy for use with influenza vaccine to improve immunization, and it is in trials in chronic hepatitis and breast and lung cancer with encouraging results.

Based upon its immunopharmacology, Thymosin $\alpha_1$ promotes T lymphocyte function, but none of the defined thymic peptides including Thymosin $\alpha_1$ have been shown unequivocally to reverse thymic involution and to increase T lymphocyte number.

Analogs and fragments of Thymosin $\alpha_1$ have been shown to have an effect upon the immune system as set forth in U.S. Pat. Nos. 4,116,951, 4,353,821, 4,466,918, 4,470,926, 4,612,365, 4,910,296. Prothymosin and Thymosin $\alpha_{11}$ also mimic some of the actions of Thymosin $\alpha_1$ and may induce its production by macrophages (Maric et al., 1991; Frillingos et al., 1992; U.S. Pat. Nos. 4,659,694, 4,716,148 and 4,614,731).

Applicants have shown that Thymosin fraction V, a crude thymic extract containing in excess of 35 peptides, has no effect by itself on thymic weight, lymphocyte content, or function in hydrocortisone-treated, aged mice. However, Thymosin fraction V augmented the effect of a natural interleukin preparation on responses of splenocytes and thymocytes to mitogens and interleukins (Hadden et al., 1992b).

It would therefore be useful to combine a natural cytokine preparation with thymic peptides, such as Thymosin $\alpha_1$, so that the combination can be used therapeutically in the treatment of diseases and other conditions which include reduced function, development and number of T lymphocytes, i.e. cellular immune deficiency.

SUMMARY OF THE INVENTION AND ADVANTAGES

The present invention provides a method to treat cellular immune deficiency in an animal or a patient by the steps of determining the presence of a cellular immune deficiency and coadministering to the patient an effective amount of a thymic peptide such as Thymosin $\alpha_1$ combined with an effective amount of a natural cytokine preparation.

BRIEF DESCRIPTION OF THE DRAWINGS

Other advantages of the present invention will be readily appreciated as the same becomes better understood by reference to the following detailed description when considered in connection with the accompanying figures wherein.

DETAILED DESCRIPTION OF THE PREFERRED EMBODIMENT

Figure 1:
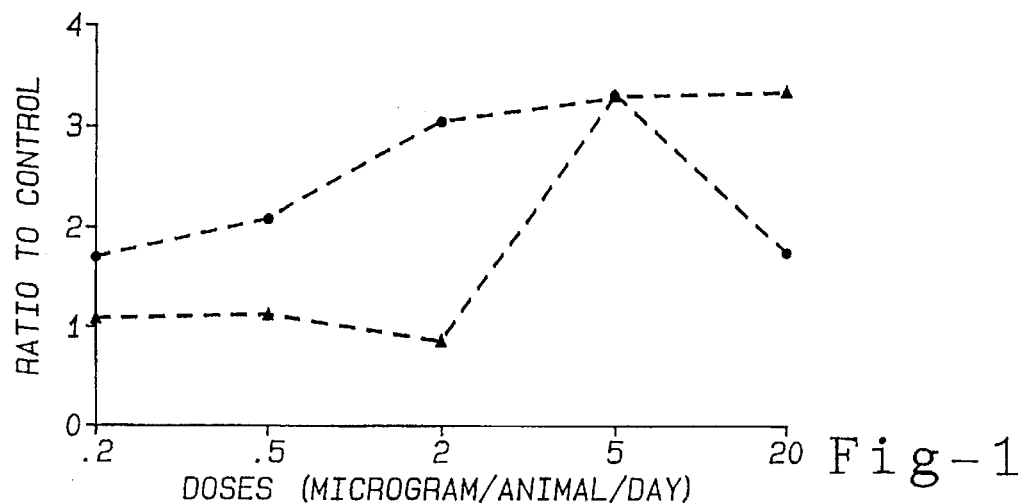
FIG. 1 is a graph of the pooled responses in vitro of thymocytes to interleukins (rIL-1, rIL-2 and NCM) and to mitogens (PHA and ConA pooled) after treatment in vivo with varying doses of Thymosin $\alpha_1$ (0.2 to 20 µg/animal/day), interleukins (—●—), mitogens (—△—)

The present invention provides a method of treating a cellular immune deficiency by co-administering a natural nonrecombinant cytokine preparation as an immunomodulator with a thymic peptide such as Thymosin $\alpha_1$. Immunomodulators are compounds that modify immune function or have a positive or negative effect on the activity of the immune system and includes cytokines.

In the preferred embodiment the immunomodulating natural nonrecombinant cytokine preparation is a natural nonrecombinant cytokine mixture (NCM) as set forth in the co-pending application by the same inventors, assigned to the assignee of the present invention, U.S. Ser. No. 08/610, 075, filed Feb. 2, 1996, which is a continuation of application Ser. No. 08/341,645, filed the same day as the present invention and incorporated by reference and as described in the Examples as set forth hereinbelow. Briefly, NCM is prepared in the continuous presence of a 4-aminoquinolone antibiotic and with continuous presence of a mitogen, which in a preferred embodiment is PHA.

However, the invention can be also be practiced with a natural nonrecombinant interleukin mixture (NIM) which is produced with the continuous presence of 4-aminoquinolone antibiotic but with only a pulsed presence of a mitogen such as PHA. Other immunomodulating natural nonrecombinant cytokine preparations, such as a NI preparation, can also be used in the present invention. The various preparations are compared by IL-2 content, and the dosage is referred to as IL-2 equivalents.

Thymic peptides are used in the present invention co-administered with the immunomodulator-cytokine preparations. Thymosin $\alpha_1$ (T-$\alpha_1$) or its analogs and fragments are used in the preferred embodiment of the present invention. In addition other thymic peptides such as thymosin $\alpha 11$ and Prothymosin and their analogs can be used. Thymic peptides, analogs and fragments that contain the thymosin $\alpha_1$ sequence can also be used.

An analog will be generally at least 70% homologous over any portion that is functionally relevant. In more preferred embodiments the homology will be at least 80% and can approach 95% homology to the thymic peptide, particularly the thymosin $\alpha_1$ sequence. The amino acid sequence of an analog may differ from that of the thymic peptide when at least one residue is deleted, inserted or substituted. Differences in glycosylation can provide analogs. Analogs as set forth in U.S. Pat. Nos. 4,116,951, 4,353,821, 4,466,918, 4,470,926, 4,612,365, 4,910,296 are examples of such analogs and can be used in the present invention.

The cellular immune deficiencies associated with aging, cancer, HIV infection, and other acute and chronic infections can be treated with the present invention. The acute and chronic infections can include, but are not limited to, tuberculosis, salmonella and leprosy.

The method of this invention involves co-administering to a mammalian host, preferably human, an effective amount of a natural nonrecombinant cytokine preparation and an effective amount of a thymic peptide such as Thymosin $\alpha_1$ (e.g., 0.6–9.6 mg/m$^2$ of body surface area) according to the invention protocol. The NCM in the preferred embodiment will have a specific cytokine profile and will generally have about 200–500 units per dose of IL-2 (IL-2 equivalents).

The patients to receive the treatment will be those with diagnosed cellular immune deficiencies either by itself or in combination with other disease states. The patient's T-cell function, development and count will be evaluated as is known in the art and, if below normal, will be a candidate for the treatment as having a cellular immune deficiency with the present invention designed to specifically treat the T-cell abnormality.

The initial dose of NCM may be administered either simultaneously with Thymosin $\alpha_1$ or by administering one drug followed by the other, generally, and preferably, on the same day. The NCM is administered at low doses (200–500 units) of IL-2 equivalence as it is important not to use high doses (>1000 units/dose) as effect is lost and toxicity increases.

The preferred combination of NCM and Thymosin $\alpha_1$ (hereinafter referred to as combination therapeutic), each individual therapeutic or other possible combinations of immunomodulating natural nonrecombinant cytokine preparations and thymic peptides such as Thymosin $\alpha_1$ and its analogs is administered and dosed in accordance with good medical practice, taking into account the clinical condition of the individual patient, the site and method of administration, scheduling of administration, and other factors known to medical practitioners. The "effective amount" for purposes herein is thus determined by such considerations as are known in the art. The amount must be effective to show improvement in immune function in 25% of patients treated including, but not limited to, improved responses in vitro measurements of cellular immune function, increased T lymphocyte levels in vivo, improved skin test response to recall antigens or NCM, improved survival rate, more rapid recovery, or improvement or elimination of symptoms and in cancer reduction of tumor mass. NCM may be used with other treatments to improve immune function and treat cancer. Example of the clinical use is exemplified by Hadden et al., (1994) in head and neck cancer.

In the method of the present invention, the combination therapeutic, or components thereof, can be administered in various ways. It should be noted that the combination therapeutic can be administered as the compound and can be administered alone or in combination with pharmaceutically acceptable carriers. The compounds can be administered, subcutaneously or parenterally including intravenous, intraarterial, intramuscularly, intraperitoneally, perilymphatic, intralymphatic, and intranasal administration. Site specific administration i.e., regional to a cancer is preferred if possible so that adjuvant effects are realized (Pulley et al, 1986; Hadden, 1994). Implants and infusions of the compounds are also useful. Guidance is provided by the reference by Talmadge et al. (1985) and Hadden et al. (1992).

For parental administration in humans, the combination therapeutic, or components thereof, will generally be formulated in unit dosage injectable form, preferably in a pharmaceutically acceptable carrier medium. Suitable carrier media include, but are not limited to, saline, squalene, dextrose solution, normal serum albumin, Ringer's solution, X-vivo 10, and the like. Optionally, minor amounts of additives such as, for example, stabilizers, preservatives or buffers may be included in such vehicle. Such formulation is suitable for reconstruction in aqueous injections for parental administration. The NCM will typically be formulated in the carrier medium at a concentration of about 50 to 500 units of IL-2 (equivalency)/ml, preferably from about 150 to 350 units of IL-2 (equivalency)/ml. The combination therapeutic will contain NCM as set forth above and will also contain 0.6–9.6 mg/m² of body surface area Thymosin-$\alpha_1$ or in an alternative embodiment the NCM will be co-administered with the Thymosin-$\alpha_1$. Further the NCM will have a consistent profile for other cytokines.

In the preferred embodiment, wherein PHA is used as the mitogen, the cytokine profile for the NCM has a profile of:

| CYTOKINE | AMOUNT |
| --- | --- |
| IL-1 | 10–2000 pg/ml |
| IL-2 | 100–500 units/ml |
| IL-6 | 250–10,000 pg/ml |
| IL-8 | 12,000–100,000 pg/ml |
| IL-12 | 100–10,000 pg/ml |
| IFN-γ | 50–15,000 pg/ml |
| TNF-α | 50–15,000 pg/ml |
| CSF-G | 50–1500 pg/ml |
| CSF-GM | 10–1500 pg/ml |
| IL-3/IL-4/IL-7 | Trace Amounts |

Optionally, the combination therapeutic, or components thereof may be brought into a sterile, stable lyophilized formulation in which the active ingredients are admixed with a water-soluble carrier, and optionally, stabilizer or non-toxic preservatives. These various additives which enhance the stability, sterility, and isotonicity of the compositions, including antimicrobial preservatives, antioxidants, chelating agents, and buffers, can be added. Prevention of the action of microorganisms can be ensured by the presence of ciprofloxacin and other antibacterial or antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, additive, or delivery vehicle used would have to be compatible with the compounds and not alter the biological activity of the present invention.

The dose and dosage regimen will depend mainly on the mammalian host, the history of the host, the type and magnitude of biological damage to the host and whether or not the components of the combination therapeutic are administered separately or in mixture, the length of treatment and the protocol of the treatment. The doses may be single dose or multiple doses over a period of several days. The most preferred doses are those which achieve regression of all measurable disease in the case of cancer. It is noted that humans are treated generally longer than the mice exemplified herein which treatment has a length proportional to the length of the disease process and drug effectiveness.

Two treatment protocols are currently under study in man with NIM. One involves a 10 day treatment protocol with NEM (at 200 units of IL-2 equivalence/day) prior to removal of the head and neck or breast cancer. The other involves 7 or more 10 day treatments as part of 21 day cycles of treatment. Both of these protocols are exemplified in Hadden et al., (1994). The combination medication with Thymosin $\alpha_1$ could be employed in the same way.

A pharmacological formulation of the combination therapeutic, or components thereof, can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as polymer matrices, liposomes, and microspheres. An implant suitable for use in the present invention can take the form of a pellet which slowly dissolves after being implanted or a biocompatible delivery module well known to those skilled in the art. Such well known dosage forms and modules are designed such that the active ingredients are slowly released over a period of several days to several weeks.

For example, such slow release forms on infusion delivery systems would be envisioned to be employed in lung and esophageal cancer so as to deliver the combination medication herein described to the regional nymph nodes in the vicinity of cancer. Other cancers would use similar regional delivery techniques.

Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well known to those skilled in the art.

When the combination therapeutic, or components thereof, is used in treatment of the immunodeficiency associated with cancer in humans, the dosage level of the NCM is generally equivalent to IL-2 content of 150 to 500 units/day. If doses are too high, the effects of the peri- and intralymphatic route may be lost. If multiple doses are administered, the frequency of administration will depend on the type of host and type of cancer, dosages and sequence of administration. For example, for some types of cancer daily administration may be effective, whereas for others, rest periods may be necessary between administration.

The medical practitioner skilled in treating immunodeficiencies will be able to ascertain upon routine examination of host and immunodeficiency, and without undue experimentation which resting periods, route of administration, frequency and duration of administration are most effective in any particular case.

In one preferred regimen, the combination therapeutic components are administered daily to a human patient in an amount of NCM equivalent to about 200 units IL-2 and substantially, simultaneously with thymic peptides such as Thymosin $\alpha_1$, analogs of Thymosin $\alpha_1$ or prothymosin at a dose range of 0.6–9.6 mg/m² of body surface area, with the preferred dose being approximately 1.2 mg/m².

The combination therapeutic is effective to increase thymocyte numbers and function and to reverse secondary immunodeficiency. It can also be used to promote initial development in the neonatal period or following irradiation or bone marrow transplantation for severe combined immunodeficiency disease (SCID) or leukemia. Alternatively, it may be useful with antiviral treatment to produce new virus free CD4+T lymphocytes in HIV-infected patients. Still, further, the inventive protocol may provide beneficial results for other non-tumor diseases associated with immunosuppression or immunodeficiency, including, for example, that associated with symptoms of aging.

The method may be used to treat patients on an in-patient as well as out-patient basis, the latter being preferable.

The above discussion provides a factual basis for the utilization of a combination therapeutic of a natural nonrecombinant cytokine preparation such as NCM and thymic peptide such as Thymosin-α. The methods used with and the utility of the present invention can be shown by the following examples.

The examples which follow demonstrate the invention in the murine system. The mouse system was chosen because, besides man, the mouse is the best studied species for structure and function of the immune system and is accepted by those skilled in the art as being highly predictive of human response. So far, only minor differences have been observed between mice and man (Chirigos and Talmadge, 1985; Talmadge et al., 1985; Hadden et al. 1992a). Most of the mechanisms by which the mouse defends itself against various pathogens and tumors are essentially the same as for man. Mouse models have been extensively employed in the evaluation of immunomodulators for use in humans. (Hadden et al., 1992a; Talmadge et al., 1985) Because of this prior art, results from current murine experiments are predictive of human responses.

Three examples demonstrate the predictive nature of the murine system with immunomodulators. Using a broad spectrum of murine tumor models the antitumor activity of interferons (IFNs) has been shown (Borden, 1979; Talmadge et al, 1985) and correspondingly in humans, IFNs have shown activity against a large variety of tumors (Goldstein and Laslo, 1988).

In a second example, using murine tumor models there was no effect of levamisole used alone on tumors but activity was seen following chemotherapy (Symoens and Rosenthal, 1977; Spreafico, 1980). Similarly in humans, levamisole showed activity in human colon cancer when used with 5 fluorouracil, but not alone (Mutch and Hutson, 1991).

In a third example, using murine tumor models low dose interleukin 2 (IL-2) was shown to have antitumor activity without toxicity while high dose IL-2 had activity especially with lymphokine activated killer (LAK) cells (Rosenberg et al, 1985), but with potentially lethal toxicity. Human studies also showed the effectiveness of high dose IL-2±LAK cells in malignant melanoma and renal cell cancer but with great toxicity (Rosenberg, 1994). It is now licensed by the FDA for renal cell cancer. Recent studies show effectiveness of low dose IL-2 in human cancer without toxicity (Cortesina et al., 1988 and 1994). The mechanisms are similar to the low dose effect of IL-2 seen in the murine system (Chirigos and Talmadge, 1985).

The above three examples of immunomodulators are now approved for clinical use in cancer and were well predicted by murine tumor studies.

In addition, animal studies have shown effects of natural nonnecominant interleukin mixtures (nILs) not shared by recombinant interleukins (rILs). nILs, but not rIL-2, are active to restore and promote thymus dependent immune responses (Hadden, et al, 1992b) and to promote resistance to malignant melanoma with cyclophosphamide. (Kameda, et al, 1992) This same pattern has been seen in humans in that natural ILs were active in human head and neck cancer in a way not shared by recombinant rIL-2. (Cortesina et al., 1988 and 1994; Hadden, et al, 1994; Mattijissen et al., 1991)

EXAMPLES

In the examples set forth below the natural nonrecombinant interleuken preparation is NCM and/or NIM used at equivalent IL-2 concentrations to provide equivalent biological activity. For simplicity, the data has been pooled and is expressed as NCM hereinafter.

General Methods

All steps relating to cell culture are performed under sterile conditions. General methods of cellular immunology not described herein are performed as described in general references for cellular immunology techniques such as Mishell and Shiigi (1981) and as are known in the art.

Materials

Thymosin fraction V (TF5) and purified Thymosin-$\alpha_1$ were gifts from Dr. A. Goldstein, George Washington School of Medicine (Washington, D.C.). Bovine TF5 is known to contain a number of thymic peptides including Thymosin-$\alpha_1$, thymopoieten and thymulin.

Recombinant human interleukin beta 1 (rIL-1 beta) was a gift from Dr. C. Reynolds, Biological Response Modifiers Program, NCI (Frederick, Md). Human interleukin 2 (IL-2; specific activity 640 U/ml) was obtained from Pharmacia AB (Silver Spring, Md.). Ciprofloxacin was purchased from Miles Inc., (West Haven, Conn.); Ofloxacin from McNeil (Spring House, Pa.); and Norfloxacin from Merck & Co (West Point, Pa.). Human serum albumin (HSA) was obtained from Armour Pharmaceuticals (Kankakee, Ill.). X-vivo media was purchased from Whittaker Bioproducts. Hydrocortisone 21-hemisuccinate and Con A were purchased from Sigma Chemicals (St. Louis, Mo.). PHA (HA-16) was obtained from Murex Diagnostics Ltd., Dartford, U.K.). OKT3 was purchased from Ortho Pharmaceuticals (Raritan, N.J.).

Preparation of Natural Nonecombinant Cytokine Preparations

The buffy coat white cells of human blood from multiple HIV-negative hepatitis virus-negative donors is collected. In an alternative embodiment, animals could be the cell source for veterinary uses. The cells from the donors are pooled and layered on ficoll hypaque gradients (Pharmacia) to yield lymphocytes free of neutrophils and erythrocytes. (U.S. Pat. Nos. 4,390,623 and 4,448,879) Alternative methods could be used that would result in the same starting lymphocyte population as are known in the art.

In a preferred embodiment for the production of NCM lymphocytes are washed and distributed in X vivo-10 media (Whittaker Bioproducts) to flasks (MicroCELLector™ T-25 Cell Culture Flasks) in which are immobilized stimulants, i.e. mitogens. In an alternate embodiment, X vivo-15 and X vivo-20 media have been used with X vivo-15 preferred over X-vivo-20. The immobilization process for the stimulants is as described by the manufacturer for immobilizing various substances for panning procedures, i.e. separating cells, in the flasks.

The cells are incubated for 24-48 hours in X vivo-10 media with 80 µg/ml ciprofloxacin (Miles Lab) at 37° in a $CO_2$/air incubator. Alternatively, minimal essential media (MEM) or RPMI 1640 media could be used (Webb et al., 1973). Following incubation the supernatants are poured off and collected. Human serum albumin (HSA) can be added to stabilize the interleukins. Generally the HSA is used at 0.1 to 0.5% (weight by volume). The supernatants are stored at 4° C. to −70° C.

Alternatively, NI can be prepared as set forth in Hadden et al., 1989 or NIM as set forth in the co-pending application in which a pulsed exposure to the mitogen is utilized.

Characterization of Supernatants

The pooled supernatants are characterized by measuring the cytokine content by bioassay for IL-2 and ELISAs for one or more of the interleukins IL-1-IL-15, CSFs, TNFs, and IFNs. Sterility is tested by culture in thioglycolate broth and endotoxin measured by limulus lysate assay as is known in the art.

Standardization of Supernatant for Cytokine Content

Each supernatant is standardized either by concentration or amount administered so that comparisons can be made. In particular the IL-2 equivalence for each supernatant is utilized.

Removal of Contaminants for Supernatant

DNA and virus exclusion, if used, will employ such techniques as ultrafiltration, ethanol fractionation, polyethylene glycol/bentonite precipitation, and/or solvent/detergent treatment as has been used for intravenous gamma globulin (IGIV News Update brochure). Photochemical inactivation, aluminum phthalocyanine, or gamma irradiation may be used.

Model

The model of hydrocortisone induced thymic involution in aged mice was used unless otherwise indicated (Hadden et al., 1992b).

Laboratory Animals

Female BALB/c (Life Science, St. Petersburg, Fla.) aged retired breeder mice (8–9 months) whose thymuses had begun to involute were employed in in vivo tests. Mice were weight matched and randomly pooled in groups of five. Animals were fed standard laboratory diets with drinking water ad lib. All mice, with exception of a control group, were treated intraperitoneally (i.p.) with hydrocortisone (5 mg/mouse in 0.1 ml 0.9% sodium chloride) for two consecutive days to induce a chemical thymectomy and reduction of spleen weight.

Hydrocortisone-treated adult mice show acute thymic involution (less than 30% of control) and reduction in spleen size (less than 80% of control) at two days with progressive recovery to 10 days. This model combines features of stress and age related thymic involution.

Experimental Design

Each treatment group had five (5) animals and each experiment was repeated 2–5 times. Treatment was initiated intraperitoneally (i.p.), on Day 3 and continued once per day for a total of five (5) days. Treatment groups were injected with one of the following in vivo treatments as indicated in the text:

1. pyrogen free saline (controls);
2. Thymosin fraction alpha 1 (TF $\alpha_1$; dose as indicated in text);
3. Thymosin fraction 5 (TF5; 100 µg/mouse);
4. natural cytokine mixture (NCM; 50 units IL-2 equivalence);
5. NCM+TF5 (at 50 units and 100 µg respectively); and
6. NCM+Thymosin $\alpha_1$ (at 50 units and 5 mg respectively);

On day 8, the mice were weighed, sacrificed by cervical dislocation, and their spleens and thymuses removed and weighed. The organs were minced, the residual erythrocytes were lysed using ammonium chloride (Mishell and Shiigi, "Selected Methods in Cellular Immunology", 1981), and the cells counted.

The proliferative response of the cells to various substances was then determined. A sample of cells was prepared for cell culture at 37° C., 5% $CO_2$ in RPMI 1640 medium with 5% fetal bovine serum, penicillin (100 U/ml), streptomycin (100 µg/ml) and 2-mercaptoethanol ($2 \times 10^{-5}$M). The cells were plated in 0.2 ml microwell plates in quadruplicate at a concentration of $1.5 \times 10^6$/ml and incubated for 72 hours with one of the following as indicated in the text:

1. control diluent (complete RPMI 1640 medium);
2. rIL-1 (1 ng/ml);
3. rIL-2 (16 Units/ml);
4. NCM (2 Units/ml of IL-2 equivalence);
5. concanavalin A (Con A; 1.5 µg/ml); and
6. phytohemagglutinin (PHA; 0.5 µg/ml).

To measure DNA synthesis, the culture was terminated with an 18 hours pulse of tritiated thymidine ($^3$H-Thymidine; NEN, Boston, Mass.; specific activity 6.7 Ci/mM), harvested with a multiple automatic sample harvester and processed for liquid scintillation counting. The results were expressed as arithmetic mean of cpm from four samples. In order to simplify the representation of data obtained with different animals, the results were pooled and calculated together and in some cases expressed as a ratio to control±SEM.

Statistical Analysis

Student's T test was used to analyze data as appropriate.

Example 1

In a series of experiments, mice with involuted thymuses were treated in vivo with NCM, Thymosin $\alpha_1$, Thymosin fraction V, combinations of these factors, and saline or media controls. The spleens and thymuses were removed, the cells were tested for cell proliferation responses to stimulation in vitro with the interleukins ($IL_1$, $IL_2$, NCM) or with mitogens (PHA; ConA).

Figure 2:
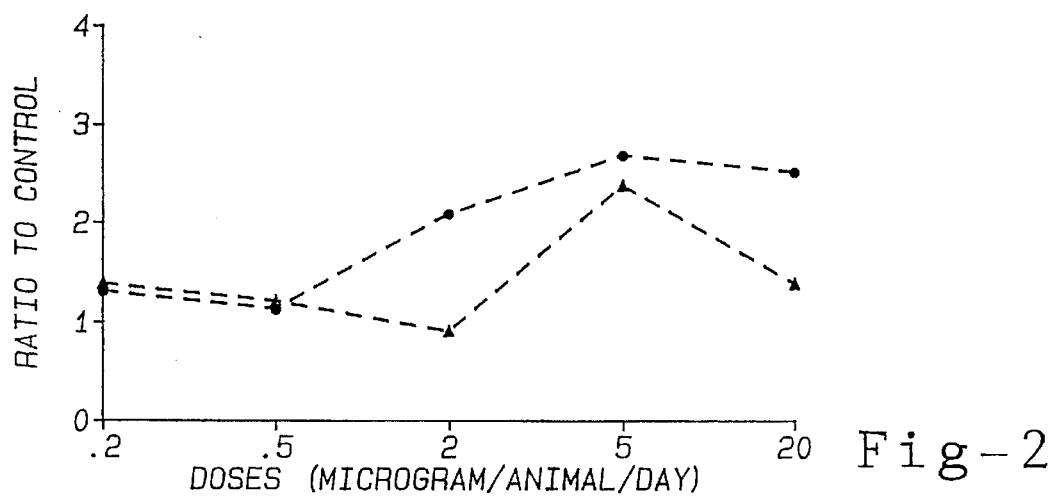
FIG. 2 is a graph of the pooled responses in vitro of splenocytes to interleukins (rIL-1, rIL-2 and NCM) and mitogens, (PHA and ConA) after treatment in vivo with varying doses of Thymosin $\alpha_1$ as in FIG. 1, interleukins (—●—), mitogens (—△—)

FIGS. 1 and 2 present the dose response curve of in vivo Thymosin $\alpha_1$ treatment on the response of thymocytes and splenocytes isolated from the treated animals to interleukins (rIL-1, rIL-2, NCM) and mitogen (PHA and ConA). The data are expressed as ratio to control; optimal effects were observed at 5µg/mouse. This value is used throughout the remaining experiments unless otherwise indicated.

In FIGS. 3–6, the results of treatment with saline (control), Thymosin $\alpha_1$ (5 µg/mouse), NCM and the combination of NCM+Thymosin $\alpha_1$ in vivo are shown.

Figure 3:
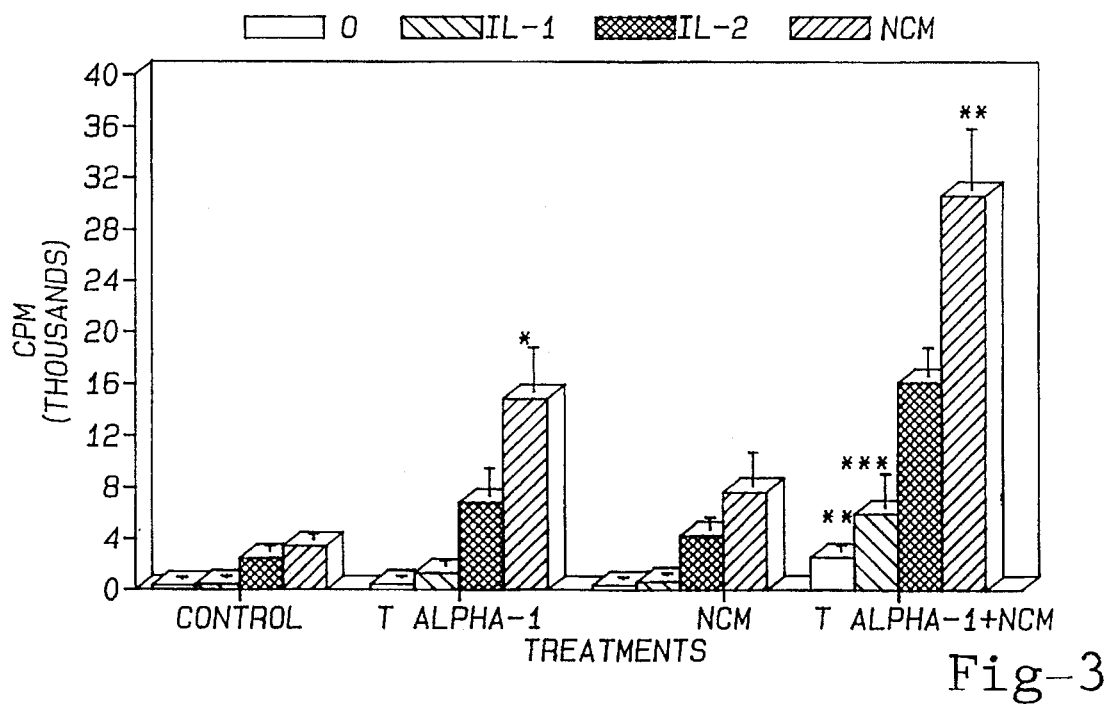
FIG. 3 is a bar graph of thymocyte responses in vitro to media (open bar), rIL-1 (closed bar), rIL-2 (cross-hatched) and NCM (diagonal lines) after treatment in vivo with saline, Thymosin $\alpha_1$ (5 µg/animal/day), NCM (50 units IL-2 equivalence) and Thymosin $\alpha_1$ (5 µg/animal/day)+NCM (50 units IL-2 equivalence)
Figure 4:
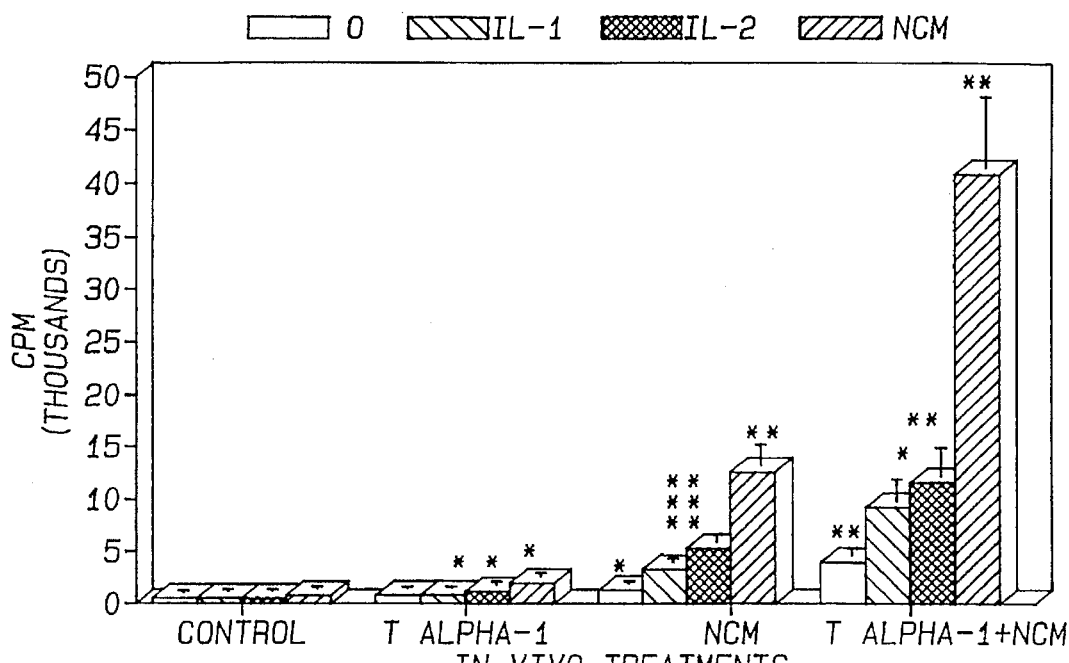
FIG. 4 is a bar graph of splenocyte responses in vitro to media (open bar), rIL-1 (closed bar), rIL-2 (cross-hatched) and NCM (diagonal lines) after treatment in vivo with saline, Thymosin $\alpha_1$, NCM and Thymosin $\alpha_1$+NCM as in FIG. 3.

In FIGS. 3 and 4, the results of these in vivo treatments on thymocyte (FIG. 3) and splenocyte (FIG. 4) responses in vitro to stimulation with media (open bars), rIL-1 (solid bars), rIL-2 (cross-hatched) and NCM (diagonal lines) are shown. Thymosin $\alpha$ and NCM alone increased many of the responses in both of the central lymphoid organs. The combination produced dramatic and highly significant increases of all four responses. These data indicate a marked sensitization of the cells to interleukin signals.

Figure 5:
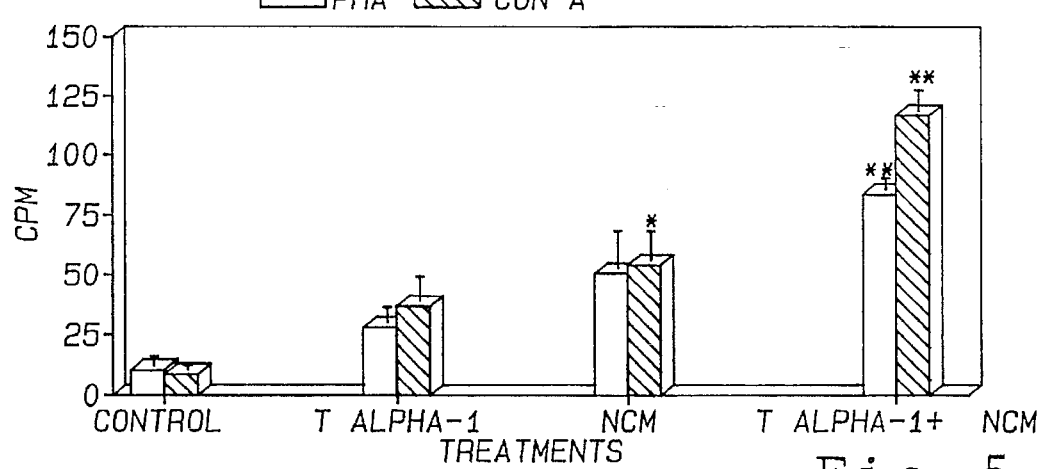
FIG. 5 is a bar graph of thymocyte responses in vitro to PHA (open bar) and ConA (closed bar) after treatment in vivo with saline, Thymosin $\alpha_1$, NCM and Thymosin $\alpha_1$+NCM as in FIG. 3.
Figure 6:
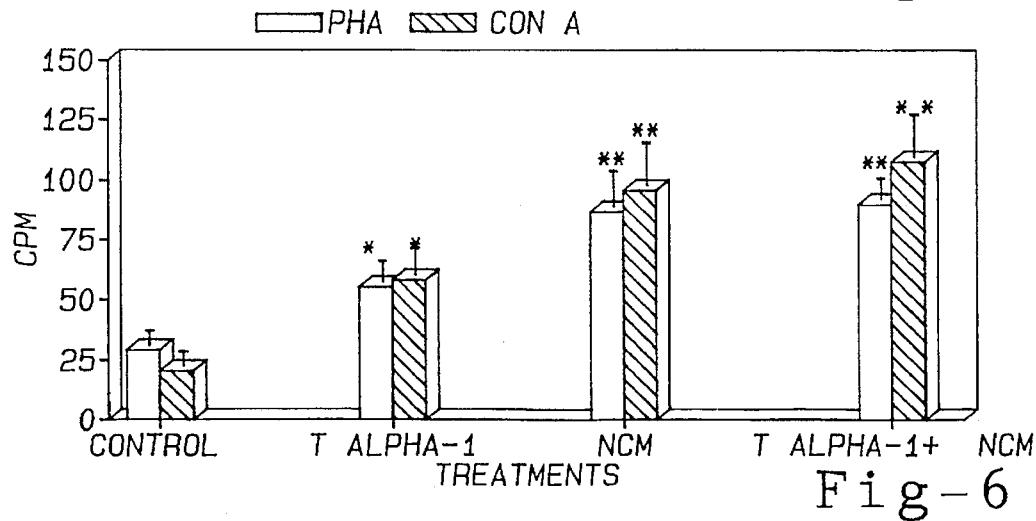
FIG. 6 is a bar graph of splenocyte responses in vitro to PHA (open bar) and ConA (closed bar) after treatment in vivo with saline, Thymosin $\alpha_1$, NCM and Thymosin $\alpha_1$+NCM as in FIG. 5.

In FIGS. 5 and 6, the results of in vivo treatments described in FIGS. 3 and 4 on thymocyte (FIG. 5) and splenocyte (FIG. 6) responses to mitogens PHA (open bars) and ConA (solid bars) are displayed. Thymosin $\alpha_1$ and NCM alone significantly augmented both responses and the combination produced marked and highly significant increases in both responses. These increases may reflect in part increased numbers of mature T cells; however, the magnitude of the increases far exceeds any possible increase in cell number (see Table IV and V hereinbelow) and thus indicates the responsiveness of these cells is greatly augmented.

Figure 8:
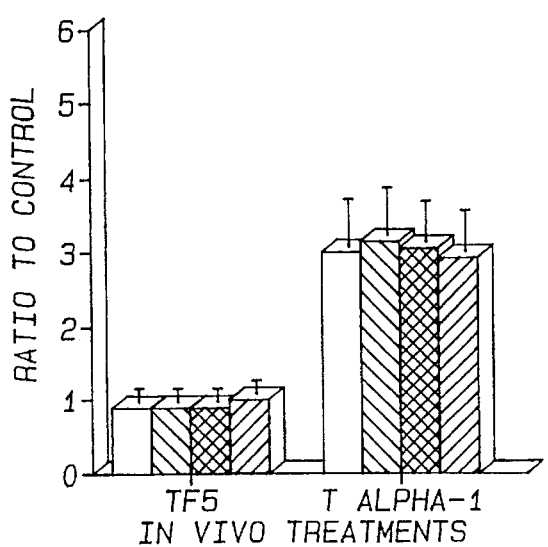
FIG. 8 is a bar graph of splenocyte responses in vitro to rIL-1 (open bar), rIL-2 (closed bar), NCM (cross-hatched) and Con A (diagonal lines) after treatment in vivo with Thymosin $\alpha_1$ (5 µg/mouse) and Thymosin fraction V (TF5, 100 µg/mouse) as in FIG. 7.
Figure 9:
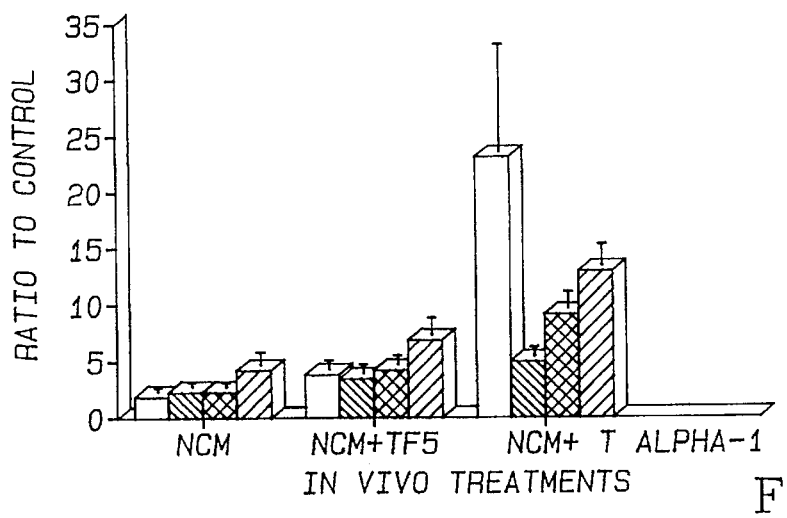
FIG. 9 is a bar graph of thymocyte responses in vitro to rIL-1 (open bar), rIL-2 (closed bar), NCM (cross-hatched) and Con A (diagonal lines) after treatment in vivo with NCM, NCM+Thymosin fraction V (100 µg/mouse) and NCM+Thymosin $\alpha_1$ (5 µg/mouse) compared to the saline treated control.
Figure 10:
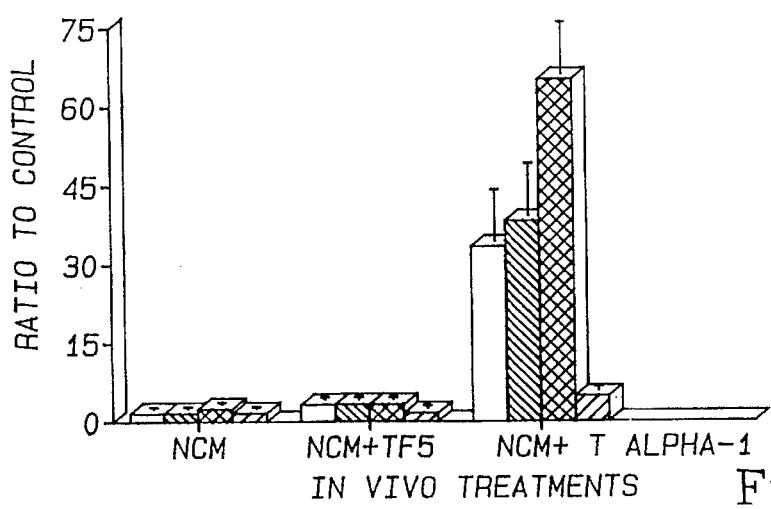
FIG. 10 is a bar graph of splenocyte responses in vitro to rIL-1 (open bar), rIL-2 (closed bar), NCM (cross-hatched) and Con A (diagonal lines) after treatment in vivo with NCM, NCM+Thymosin fraction V (100 μg/mouse) and NCM+Thymosin $\alpha_1$ (5 μg/mouse) compared to the saline treated control.

Further experiments were performed to determine the difference in response to treatment in vivo with Thymosin fraction V or Thymosin $\alpha_1$ alone (FIGS. 7 and 8) compared to the combination of NCM and Thymosin fraction V or Thymosin $\alpha_1$ (FIGS. 9 and 10).

Figure 7:
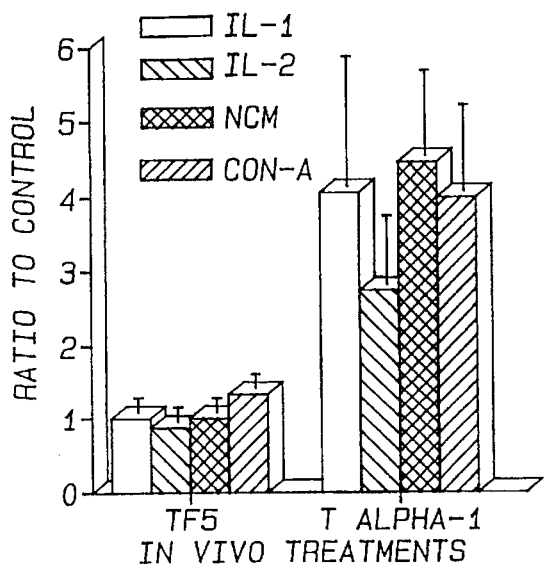
FIG. 7 is a bar graph of thymocyte responses in vitro to rIL-1 (open bar), rIL-2 (closed bar), NCM (cross-hatched) and Con A (diagonal lines) after treatment in vivo with Thymosin $\alpha_1$ (5 µg/mouse/day) and Thymosin fraction V (TF5, 100 µg/mouse/day) expressed as a ratio to the saline treated control.

In FIGS. 7 and 8, Thymosin fraction V (TF5) had no effect alone on splenocytes (FIG. 8) and thymocyte (FIG. 7) responses to rIL-1 (open bar), IL-2 (solid bar), NCM (cross-hatched bar) or ConA (diagonal lines) as reported by Hadden et al. (1992). In contrast, Thymosin $\alpha_1$ (5 µg/ml) augmented all of the responses in both splenocytes and thymocytes.

In FIGS. 9 and 10, the effect of NCM and the combined effect of NCM plus Thymosin fraction V (TF5) or NCM plus Thymosin $\alpha_1$, on thymocyte (FIG. 9) and splenocyte (FIG. 10) responses to rIL-1 (open bar), or IL-2 (solid bar) NCM (cross-hatched bar) or ConA (diagonal lines) is shown. The effects of Thymosin $\alpha_1$ in combination with NCM are much greater than those of Thymosin fraction V. This unexpected finding indicates that Thymosin $\alpha_1$ has unique immunopharmacologic features not previously described for any thymic hormone preparation (pure or extracted peptides).

The unexpected, striking effects of the combination of Thymosin $\alpha_1$ with NCM on the stimulation of T lymphocyte responses in these two central lymphoid organs are unique as they suggest that intraperitoneal injection has sensitized the entire system to stimulation with cytokines and mitogens. In many cases, the interaction of NCM and Thymosin $\alpha_1$ is more than additive (i.e. synergistic) and the magnitude of these effects was unexpected based on the prior art. It was also unexpected that thymosin $\alpha_1$ was active by itself Example 2

The effect of NCM and Thymosin $\alpha_1$ on both spleen and thymus responses weights are shown in Table IV.

Animals, hydrocortisone treatment, and experimental injections were as described in the general methods. The NCM was injected at 50 U of IL-2 per mouse/day. The Thymosin $\alpha_1$ (T alpha-1 or T$\alpha$1) was injected at 5 or 20 microgram/mouse/day. These experiments were found to be equivalent and were thus pooled.

TABLE IV

| | SPLEEN WEIGHT (mg) | | | |
|---|---|---|---|---|
| Group | Mean ± S.E.M. | n | # of Expts. | Vs. Control |
| Control | 125.98 ± 2.40 | 100 | 21 | |
| NCM | 138.38 ± 3.03 | 88 | 18 | $p < .05$ |
| T$\alpha$1 | 127.66 ± 5.78 | 29 | 5 | N.S. |
| NCM + T$\alpha$1 | 165.40 ± 10.51 | 20 | 3 | $p < .01$ |

NCM vs. NCM + T alpha-1: $p < .05$

TABLE V

| | THYMUS WEIGHT (mg) | | | |
|---|---|---|---|---|
| Group | Mean ± S.E.M. | n | # of Expts. | Vs. Control |
| Control | 33.6 ± 1.77 | 84 | 18 | |
| NCM | 35.72 ± 1.80 | 85 | 18 | N.S. |
| T$\alpha$1 | 25.75 ± 4.45 | 16 | 3 | $p < .01$ |
| NCM + T$\alpha$1 | 32.95 ± 5.86 | 20 | 3 | N.S. |

NCM vs. NCM + T alpha 1: N.S.

These data indicate that NCM and Thymosin $\alpha_1$ in combination have no significant effect on thymus weight. The mature T-cells in thymus (CD4$^+$ and CD8$^+$) averaged 27±3.5% in the control and 32.5±in the NCM and Thymosin alpha 1 treated mice. The mature T-cells in spleen (CD4$^+$ and CD8$^+$) averaged 70±1% in the control and 76.5±5% in the NCM and Thymosin alpha 1 treated mice. While the small increases in the proportions of mature T-cells in the thymus and spleen were not statistically significant, when they are viewed in relationship to the significant 31% increase in spleen weight with NCM and Thymosin alpha 1 treatment it is apparent that the treatment induced a large increase in the absolute numbers of T-cells in the spleens.

The composition also potently promotes T lymphocyte function (IL responses) and development (mitogen responses), as shown in the cell proliferation assays, which is therapeutically relevant in any therapeutic measures requiring stimulation of the immune system or restoring even partial functioning of a damaged or defective immune system. For example chemotherapeutic agents can damage cells, including T lymphocytes, involved in the immune response. The present invention by stimulating T lymphocyte function and development can restore, either partially or entirely, this features of the immune system if damaged.

Throughout this application, various publications, including United States patents, are referenced by citation or number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

*The Investigator's Handbook* provided by the Cancer Therapy Evaluation Program, Division of Cancer Treatment, National Cancer Institute, pg 22

Belldegrun and Rosenberg, "Adoptive Immunotherapy of Urologic Tumors", *Cancer Treat. Res.* 46: 213–233, 1989

Borden, "Interferons: Rationale for Clinical Trials in Neoplastic Disease", *Ann. Int. Med.* 91: 492–479, 1979.

Chang and Rosenberg, "Overview of Interleukin-2 as Immunotherapeutic Agent", *Semin. Surg. Oncol.*, 5(6): 385–390, 1989

Chirigos and Talmadge. Immunotherapeutic Agents: Their Role in Cellular Immunity and Their Therapeutic Potential. *Springer Seminars in Immunopathol.* 8: 327–336, 1985.

Cortesina et al., "Treatment of Recurrent Squamous Cancer Cell of Head and Neck with Low Doses of Interleukin 2 Injected Perilymphatically" *Br. J. Cancer* 62: 2482–2485, 1988

Cortesina et al., "Temporary Regression of Recurrent Squamous Cell Carcinoma of the Head and Neck is Achieved with a Low but not with a High Dose of Recombinant Interleukin 2 Injected Perilymphatically" *Br. J. Cancer* 69: 572–576, 1994

DeSimone et al, "Report of the Symposium on the Use of Intravenous Gammaglobulin (IVIG) in Adults Infected with HIV", *J. Clin. Lab. Anal.* 4: 313–317, 1990.

Devos et al. "Molecular Cloning of Human Interleukin 2 cDNA and Its Expression in *E. coli*" *Nucleic Acids Res.*, 11: 4307–4323, 1983

Frillingos et al., "Appearance of Thymosin $\alpha_1$ in Supernatants of Monocytes Incubated with Prothymosin $\alpha$" *Archives of Biochemistry and Biophysics*, Vol. 296, No. 1, July, pp. 356–263, 1992

Goldstein et al.,"Tymosin $\alpha_1$: Isolation and Sequence Analysis of an Immunologically Active thymic Polypeptide" *Proc. Natl. Acad. Sci.*, 74(2): 725–729, Feb. 1977

Goldstein and Laslo, "The Role of Interferon in Cancer Therapy: A Current Perspective", *Ca-A Cancer Journal For Clinicians* 38: 258–290, 1988.

Goldstein "Thymosin $\alpha_1$: Chemistry, Mechanism of Action and Clinical Applications" in *Combination Therapies 2*, pp 39–48, Plenum Press, N.Y., 1993

Hadden et al., "Strategies of Immune Reconstitution: Effects of Lymphokines on Murine T Cell Development in vitro and in vivo", *Life Sci.* 44: 5–12, 1989

Hadden "Immunotherapy of Human Immunodeficiency Virus Infection", *TIPS Reviews*, 1991

Hadden, "Thymic Endocrinology" *Int. J. Immunopharmacol.*, 14: 345–352, 1992

Hadden and Smith, "Immunopharmacology" *JAMA*, 268: 2964–2969, 1992

Hadden et al., "The Characterization of Immunotherapeutic Agents" *Immunopharmacol Reviews* 1: 1–64, 1992a Hadden et al., "Mixed Interleukins and Thymosin Fraction V Synergistically Induce T Lymphocyte Development in Hydrocortisone-Treated Aged Mice" *Cell. Immunol.* 144: 228–236, 1992b Hadden "Immunostimulants" *Immunology Today* 276, Vol 14, No. 6, 1993

Hadden et al., "Interleukins and Contrasuppression Induce Immune Regression of Head and Neck Cancer" *Int. Arch. Otolaryngol.* 120: 395–403, 1994

Hall, "Immunomodulation with intravenous immunoglobulin" *Pharmacotherapy*, 13(6): 564–73, Nov–Dec, 1993

Hwu and Rosenberg, "The Genetic Modification of T Cells for Cancer Therapy: An Overview of Laboratory and Clinical Trials", *Cancer Detect. Prev.* 18(1): 43–50 1994b.

Hwu and Rosenberg, "The Use of Gene-Modified Tumor-Infiltrating Lymphocytes for Cancer Therapy", *Ann. N.Y. Acad. Sci.* 716: 188–203 1994a.

*IGIV News Update*, "An Extra Measure of Viral Safety", Vol.1, No.2, December 1993

Kameda et al., "Mixed Lymphokines in Low Dose Prolong Life in Cyclophosphamide-Treated Melanoma-Bearing Mice", *Int. J. Immunother.* 8: 1–5, 1992.

Lane and Fauci, "Therapeutic Approaches to the Undulying Immune Deficit in AIDS" *Abstracts Int. Conf. on AIDS*, Paris 1986

Maric et al., "in vivo Effect of Prothymosin-alpha on Humoral and Cell Mediated Immunity in the Young Rat", *Int. J. Neurosci*, 59: 135–142, 1991

Mattijissen, "Clinical and Immunopathological Results of a Phase II Study of Perilymphaatically Injected Recombinant Interleukin-2 in Locally Far Advanced, Nonpretreated Head and Neck Squamous Cell Carcinoma. *J. Immunother.* 10: 63–68, 1991.

Merigan, "Combination Anti-HIV Therapy: Questions and Ansers" in *Combination Therapies 2*, eds. Goldstein and Garaci, Plenum Press, pp. 225–229 1993.

Mishell and Shiigi, Selected Methods *Cellular Immunology*, Freeman, pp. 23–24, 1981

Morgan et al. "Selective in vitro Growth of T Lymphocytes from Normal Human Bone Marrows" *Science*, 193: 1007–8, 1976

Mule and Rosenberg, "Mechanistic Aspects of Successful Immunotherapy . . .", *Prog. Clin. Biol.*, 244: 79–91, 1987

Mutch and Hutson, "Levamisole in the Adjuvant Treatment of Colon Cancer", *Clin. Pharmacol.* 10: 95–109, 1991

Pulley et al., "Intravenous, Intralesional and Endolymphatic Administration of Lymphokines in Human Cancer" *Lymphokine Research*, Vol. 5, Supplement 1, pp. S157–S163 1986

Rosenberg et al., "Observations on the Systemic Administration of Autologous Lymphokine-Activated Killer Cells and Recombinant Interleukin-2 to Patients with Metastatic Cancer", *New Eng. J. Med.* 313: 1485–1492, 1985.

Rosenberg et al., "A Progress Report on the Treatment of 157 Patients with Advanced Cancer using Lymphokine-Activated Killer Cells and Interleukin-2 or High-Dose Interleukin-2 Alone" *N. Engl. J. Med.* 316: 889–897, 1987

Rosenberg. "Immunotherapy of Cancer by Systemic Administration of Lymphoid Cells Plus Interleukin-2." *J. Biol. Resp. Mod.* 3: 501–511, 1994.

Shuloff, "Thymic Peptide Hormones: Basic Properties and Clinical Applications in Cancer" *CRC Critical Reviews in Oncology/Hematology*, 3: 3309–376, 1985

Spreafico, "Use of Levamisole in Cancer Patients", *Drugs* 19: 105–116, 1980.

Symoens and Rosenthal, "Levamisole in the Modulation of Immune Response: The Current Experimental and Clinical State", *J. Reticuloendothel. Soc.* 21: 175–219, 1977.

Talmadge et al., Screening for Biological Response Modifiers: Methods and Rationale, Martinus Nijhoff, Boston, p. 121–129 & 181–182, 1985.

Taniguchi et al. "Structure and Expression of a Cloned cDNA for Human Interleukin-2" *Nature*, 302: 305–310, 1983

Webb et al., "Mitogen-Induced Human Lymphocyte Activation in Serum-Free Medium" *Clinical Immunology and Immunopathology*, 1: 304–310 1973

What is claimed is:

1. A method of improving cellular immune response in a patient comprising
coadministering to the patient an effective amount of a peptide selected from the group consisting of Thymosin $\alpha_1$, Thymosin $\alpha_1$ analogs and Thymosin $\alpha_1$ fragments and an effective amount of a cellularly-produced non-recombinant cytokine preparation wherein the nonrecombinant cytokine preparation contains a cytokine profile of IL-1 at 10–2000 pg/ml, IL-2 at 100–500 units/ml, IL-6 at 250–10,000 pg/ml, IL-8 at 12,000–100,000 pg/ml, IL-12 at 100–10,000 pg/ml, IFN-γ at 50–15,000 pg/ml, TNF-γ at 50–15,000 pg/ml, CSF-GM at 10–1560 pg/ml, and IL-3, IL-4, IL-7 present in trace amounts.

2. The method of claim 1 wherein the thymosin peptide is Thymosin $\alpha_1$.

* * * * *